(12) United States Patent
Remington et al.

(10) Patent No.: US 7,041,309 B2
(45) Date of Patent: *May 9, 2006

(54) SPINAL FUSION USING AN HMG-COA REDUCTASE INHIBITOR

(75) Inventors: Benjamin J. Remington, Modesto, CA (US); David J. Bearss, Tucson, AZ (US); Kavian Shahi, Granite Bay, CA (US)

(73) Assignee: NeuroPro Technologies, Inc., Modesto, CA (US)

( * ) Notice: Subject to any disclaimer, the term of this patent is extended or adjusted under 35 U.S.C. 154(b) by 633 days.

This patent is subject to a terminal disclaimer.

(21) Appl. No.: 10/282,338

(22) Filed: Oct. 28, 2002

(65) Prior Publication Data

US 2003/0232065 A1    Dec. 18, 2003

Related U.S. Application Data

(60) Provisional application No. 60/388,222, filed on Jun. 13, 2002, provisional application No. 60/394,791, filed on Jul. 10, 2002.

(51) Int. Cl.
*A61F 2/28* (2006.01)

(52) U.S. Cl. .................. 424/426; 424/423; 424/424; 424/425; 523/113; 523/116

(58) Field of Classification Search .............. 424/423, 424/424, 425, 426; 623/16.11, 17.11; 523/113, 523/116
See application file for complete search history.

(56) References Cited

U.S. PATENT DOCUMENTS

| 4,870,063 | A | 9/1989 | Binderup et al. ............. 514/79 |
| 5,258,376 | A | 11/1993 | Bernstein .................... 514/184 |
| 5,280,040 | A | 1/1994 | Labroo et al. ............... 514/422 |
| 5,336,687 | A | 8/1994 | Sabatucci .................... 514/473 |
| 5,403,829 | A | 4/1995 | Lehtinen et al. ............ 514/102 |
| 5,462,932 | A | 10/1995 | Brenner et al. ............. 514/108 |
| 5,545,661 | A | 8/1996 | Cullinan ..................... 514/460 |
| 5,604,257 | A | 2/1997 | Tabe et al. .................. 514/460 |
| 5,935,607 | A | 8/1999 | Silver ......................... 424/601 |
| 6,022,887 | A | 2/2000 | Gasper et al. ............... 514/451 |
| 6,040,334 | A | 3/2000 | Myers et al. ................ 514/460 |
| 6,080,779 | A | 6/2000 | Gasper et al. ............... 514/451 |
| 6,083,690 | A | 7/2000 | Harris et al. .................. 435/6 |
| 6,153,212 | A | 11/2000 | Mao et al. .................. 424/426 |
| 6,207,153 | B1 | 3/2001 | Dan et al. ................. 424/138.1 |

(Continued)

FOREIGN PATENT DOCUMENTS

WO    WO03105731    * 12/2003

OTHER PUBLICATIONS

"Instructions for Use: Cook-Swartz Doppler Flow Probe and Monitoring System", 1998 Cook Vascular Incorporated FM-15588 Aug. 1999.

(Continued)

*Primary Examiner*—Carlos A. Azpuru
(74) *Attorney, Agent, or Firm*—Wilson Sonsini Goodrich & Rosati

(57) ABSTRACT

An improved technique for spinal fusion including administration of an HMG-CoA reductase inhibitor to the fusion site. The HMG-CoA reductase inhibitor is preferably delivered to the site by a carrier. More preferably, the HMG-CoA reductase inhibitor is delivered to the site by a noncompressible delivery vehicle. The invention is suitable for promoting non-anatomic or heterotopic bone growth between any bony surfaces where bone growth is desired but does not naturally occur.

26 Claims, 8 Drawing Sheets

U.S. PATENT DOCUMENTS

| | | | |
|---|---|---|---|
| 6,322,797 B1 | 11/2001 | Mao et al. ................... | 424/271 |
| 6,369,109 B1 | 4/2002 | Debatin et al. ............. | 514/569 |
| 6,376,476 B1 | 4/2002 | Gasper et al. .............. | 514/100 |
| 6,376,644 B1 | 4/2002 | Mao et al. ................... | 528/398 |
| 6,403,637 B1 | 6/2002 | Partridge .................... | 514/455 |
| 6,462,019 B1 | 10/2002 | Mundy et al. ................ | 514/12 |

OTHER PUBLICATIONS

Pilitsis, M.D., Julie G. et al., "Bone Healing And Spinal Fusion," *Neurosur. Focus 13* (6); Article 1, vol. 13, (2002), pp. 1-6.

Csizy, M. et al., "Displaced Intra-Articular Calcaneal Fractures" *Journal of Orthopaedic Trauma*, vol. 17, No. 2, pp. 106-112.

Edwards, Richard C. et al., "Fixation of Bimaxillary Osteotomies With Resorbable Plates And Screws: Experience in 20 Consecutive Cases," *J. Oral Maxillofac. Surg.* (2001) 59: pp. 271-276.

Fadel, G.E. et al., "Hallux Metatarsophalangeal Joint Arthrodesis: Various Techniques," *The Foot*, (2002, 12, pp. 88-96.

Fearon, M.D., J., "Rigid Fixation Of The Calvaria In Craniosysnostosis Without Using "Rigid" Fixation," *Plastic And Reconstructive Surgery*, (2003) pp. 27-38.

Hendricks, M.D., R.L., "Bone Morphogenic Protein," *Annual Workers' Compensation Seminar*, (1998) pp. 1-3.

Jones, S. et al., "Arthrodesis For Failed Ankle Arthoplasty: A Technique Using The Fibula As An Autogeneous Bone Graft," *The Foot*, (1999), 9, pp. 142-144.

Mundy, G. et al., "Stimulation of Bone Formation in Vitro And In Rodents by Statins," *Science*, (1999) vol. 286, pp. 1946-1949.

Schwetlick, G. et al., "Results of Arthrodesis And Operative Stabilization of Osteotomies With A Compression Staple System," *The Foot*, (2003) pp. 100-107.

Wozney, J. M., et al., "Engineering What Comes Naturally—Tissue engineers have developed a synthetic matrix that interacts with host cells to deliver bone-inductive proteins for bone regeneration." *Nature Biotechnology*. May 2003. vol. 21: 506-508.

\* cited by examiner

SPINAL FUSION USING AN HMG-COA REDUCTASE INHIBITOR

This application claims benefit of U.S. provisional application 60/388,222 filed Jun. 13, 2002 and claims benefit of U.S. provisional application 60/394,791 filed, Jul. 10, 2002

FIELD OF THE INVENTION

The present invention relates to spinal fusion and, in particular, using an HMG-CoA reductase inhibitor to promote bone growth and bone fusion by promoting bone morphogenic protein production.

BACKGROUND OF THE INVENTION

The vertebrae are bones that make up the spinal column, which surrounds and protects the spinal cord. Nerves from the spinal cord exit the spinal column between each vertebra. Intervertebral discs are soft tissues positioned between each vertebrae. The discs act as cushions between the vertebrae by absorbing energy while the spinal column flexes, extends, and twists. The disc allows for movements of the vertebrae and lets people bend and rotate their neck and back. The type and degree of motion varies between the different levels of the spine: cervical (neck), thoracic (chest) or lumbar (low back). The cervical spine permits movement in all directions. The thoracic spine protects the heart and lungs and is more rigid than the cervical spine due to rib presence. The lumbar spine permits primarily forward and backward bending movements, flexion and extension.

Spinal fusion is a surgical technique, typically involving the use of bone graft, that causes two opposing bony surfaces to grow together (arthrodesis). In spinal fusion, one or more of the vertebrae of the spine are fused to prevent any motion therebetween. At each level in the spine, there is a disc space in the front and paired facet joints in the back. Working together, these structures define a motion segment and permit multiple degrees of motion. Two vertebral segments need to be fused to stop the motion at one segment. Generally, spinal fusion surgery involves adding bone graft to an area of the spine to prompt a biological bone growth response. The growth of bone between the two vertebrae is facilitated by the bone graft and effectively stops motion at that segment.

There are many potential reasons for spinal fusion. Example reasons include: treatment of a fractured vertebra; correction of deformity; elimination of pain from painful motion; treatment of instability; and treatment of cervical disc herniations. While not all spinal fractures need surgery, some fractures, including those associated with spinal cord or nerve injury, generally require fusion as part of the surgical treatment. In spondylolisthesis, a hairline fracture allows vertebrae to slip forward on top of each other. This condition may be treated by fusion surgery. Certain types of spinal deformity, such as scoliosis, are commonly treated with spinal fusion. Another condition treated with fusion surgery is actual or potential instability (or abnormal or excessive motion between two or more vertebrae). Cervical disc herniations requiring surgery often call for fusion as well as removal of the herniated disc (discectomy). With this procedure, the disc is removed through an incision in the front of the neck (anteriorly) and a small piece of bone is inserted in place of the disc. Although disc removal is commonly combined with fusion in the cervical spine, this is not generally true in the lumbar spine. Further, spinal fusion may be called for in the treatment of a painful spinal condition without clear instability.

It is important to note that spinal fusion surgery does not involve merely the knitting of a bone around a spinal fracture, although a spinal fracture may be the impetus for performing the spinal fusion. While a side-consequence of the spinal fusion surgery or of the natural biological response to a fracture may involve knitting of the fracture, spinal fusion involves stimulating nonanatomic or heterotopic bone growth between two vertebra to fuse the vertebra together.

Many surgical approaches and methods involving placement of a bone graft between the vertebrae can be used to fuse the spine. The spine may be approached and the graft placed either from the back (posterior approach), from the front (anterior approach) or by a combination of both approaches. The type and location of the incision for access to the spinal region depends on the area needing treatment. The lower spinal vertebrae are repaired through an incision directly over the spine (posterior lumbar approach). The upper spinal vertebrae are repaired through an incision in the back or side of the neck (cervical spine). The middle spinal vertebrae are repaired through an incision made in the chest and abdomen (anterior thoracic spine). The abnormal or injured vertebrae are repaired and stabilized with bone grafts, metal rods, other instrumentation, or a combination of the above.

There are several types of spinal fusion, including:
Posterolateral gutter fusion
Posterior lumbar interbody fusion (PLIF)
Anterior lumbar interbody fusion (ALIF)
Anterior/posterior spinal fusion
Cervical fusion
Thoracic fusion
Interlaminar fusion Posterolateral gutter fusion involves placing bone graft in the posterolateral portion of the spine (a region just outside the spine). The surgical approach to the spine is from the back through a midline incision that is approximately three inches to six inches long. Typically, bone graft is obtained from the pelvis (the iliac crest) and the harvested bone graft is laid out in the posterolateral portion of the spine. The back muscles that attach to the transverse processes are elevated to support the bone graft. The back muscles are replaced over the bone graft to create tension to hold the bone graft in place. After surgery, the body attempts to heal itself by growing bone. The growth of bone by the body grows the harvested bone graft and adheres the graft to the transverse processes. At this point, spinal fusion is achieved and motion at that segment is stopped.

Posterior lumbar interbody fusion (PLIF) involves adding bone graft to an area of the spine to set up a biological response that causes bone to grow between the two vertebrae and stop the motion at that segment. PLIF achieves spinal fusion by inserting bone graft directly into the disc space. The spine is approached through an incision (typically three to six inches long) in the midline of the back and the left and right erector spinae are stripped off the lamina on both sides and at multiple levels. After the spine is approached, the lamina is removed (laminectomy) to allow visualization of the nerve roots. The facet joints, which are directly over the nerve roots, are trimmed to make more space for the nerve roots. The nerve roots are retracted to one side and the disc space is cleaned of the disc material. A bone graft, or interbody cage with bone, or other instrumentation or implant, is inserted into the disc space and the bone grows from vertebral body to vertebral body.

Anterior lumbar interbody fusion (ALIF) is similar to the PLIF, except that in ALIF the disc space is fused by approaching the spine through the abdomen instead of through the back. In the ALIF approach, an incision (typically three to five inches) is made on the left side of the abdomen and the abdominal muscles are retracted to the side. The peritoneum can also be retracted to allow the surgeon access to the front of the spine. Some ALIF procedures are done using a minilaparotomy (one small incision) or with an endoscope (a scope that allows the surgery to be done through several one-inch incisions). Regardless of the specific procedure, the aorta and vena cava are moved aside, the disc material is removed and bone graft, or bone graft and anterior interbody cages, other implant, or instrumentation, is inserted.

Anterior/posterior lumbar fusion involves performing a lumbar interbody fusion and a posterolateral gutter fusion to fuse both the front and back of the spine. Fusing both the front and back provides a high degree of stability for the spine and a large surface area for the bone fusion to occur. The disc may be approached either as an ALIF or as a PLIF, and the back part of the spine is fused with a posterolateral gutter fusion.

The ultimate goal of fusion is to obtain a solid union between two or more vertebrae. This is done by causing non-anatomic growth of bone, most commonly around a bone graft, instrumentation including a bone graft, or other implant. Spine fusion involves causing bone to grow in a space where it does not normally grow, that is, in the space between two vertebra. Spine surgery instrumentation is sometimes used as an adjunct to obtain a solid fusion. This is particularly advantageous because causing non-anatomic or heterotopic growth of bone attempts to take advantage of the body's natural healing process of growing bone and yet use that process in a way that would not normally occur. Non-anatomic or heterotopic growth in this manner differs significantly from the mere knitting of a fractured bone and can be difficult to achieve. A common problem in spine fusion is that it is nonsuccessful and results in non-union. Instrumentation can decrease the likelihood of non-union by maintaining spinal stability while facilitating the process of fusion. The instrumentation can be used to bridge space created by the removal of a spinal element such as an intervertebral disc. Instrumentation is sometimes used to correct a deformity, but usually is solely used as an internal splint to hold the vertebrae together while the bone grafts heal. Such instrumentation may include titanium, titanium-alloy, stainless steel, or non-metallic devices for implantation into the spine. Instrumentation provides a permanent solution to spinal instability. Medical implants are available in many shapes and sizes. Typically these include rods, hooks, braided cable, plates, screws, and threaded interbody cages. Unfortunately, even with the use of instrumentation, non-union remains a common problem.

Regardless of whether instrumentation is used, bone or bone substitutes are used to prompt the vertebrae to fuse together. Traditionally, the surgical technique includes a grafting procedure utilizing autologous bone harvested from a separate site. In a typical procedure, bone chips from a patient's pelvic bone are transplanted, or grafted, to the spinal vertebrae to help fusion therebetween. Alternatively, allograft, bone harvested from a bone bank or other source, may be used. Similarly, synthetic and xenograft derived bone substitutes (calcium phosphate, hydroxylapatite, and/or other ceramic based bone substitutes) may be used.

Although the use of autologous bone for spinal fusion is common, harvesting bone graft from a patient's body has many disadvantages. Among other things, graft harvesting prolongs surgical time, increases blood loss, increases the risk of infection, and can be a source of chronic pain. Significantly, use of autologous bone does not always ensure successful fusion, even when used in combination with instrumentation. Inherent limitations in autogenous and allogeneic bone grafting have led to exploration of other technology, for example, using bone morphogenic protein (BMP) in spinal fusion. As an adjuvant to allograft or as a replacement for harvested autograft, BMP can improve spinal fusion.

Bone morphogenic protein (BMP) is in the bone's own matrix and has the ability to stimulate the body's own cells to produce more bone. Specifically, BMP can direct the repair and regeneration of bone in various parts of the skeleton. BMP can be beneficial to patients undergoing spinal fusion by eliminating the need for bone transplantation from the pelvis. BMP has been used to promote bone fusion by putting BMP on a mesh, gel, or other carrier and placing that carrier at the site where the bone fusion is desired.

To function as a suitable graft for spinal fusion—involving bridging bone defects or fusing facture lines and unstable motion segments—the graft must have three characteristics. It must provide a source of primitive osteoprogenitor cells that form osteoblasts and osteocytes (osteopromotion). The graft material must produce local growth factors to stimulate bone growth and vascularity in the area (osteoinduction). Lastly, it must act as a scaffold to bone ingrowth (osteoconduction).

BMP has a multifaceted osteoinductive role, acting as a chemotactic agent, a growth factor, and a differentiation factor. As a chemotactic factor, it initiates the recruitment of progenitor and stem cells toward the area of bone injury. As a growth factor, it stimulates both angiogenesis and the proliferation of stem cells from surrounding mesenchymal tissues. As a differentiation factor, it promotes maturation of stem cells into chondrocytes, osteoblasts, and osteocytes.

Thus far, growth and differentiation factors have been obtained in a variety of ways for application directly to a surgical site. These include: extraction of the factors from animal or human bone matrix, production of a single factor by cellular hosts by using recombinant technology, and direct delivery to cells at the site of desired bone formation of the DNA encoding for the factor.

Although BMPs are potent stimulators of bone formation, there are disadvantages to their use in enhancing bone healing. Receptors for the BMPs have been identified in many tissues, and the BMPs themselves are expressed in a large variety of tissues in specific temporal and spatial patterns. This suggests that BMPs may have effects on many tissues in addition to bone and their usefulness as therapeutic agents, particularly when administered systemically, may be limited. However, their usefulness is not only suspect when administered systemically, there are equally serious concerns regarding local administration of BMPs to a surgical site. It is difficult to control BMP's effect on bone growth and surrounding tissue. The consequences of BMP's effect on bone growth at spinal fusion sites is particularly concerning. Hypergrowth as a result of BMP application directly to a spinal fusion site may pinch nerves and result in not only pain but possibly paralysis. Consequently, it may not be desirable to apply BMP directly to a spinal fusion site.

HMG-CoA reductase inhibitors, or statins, have been known to promote BMP production. U.S. Pat. Nos. 6,080,779, 6,376,476, and 6,022,887 each disclose using HMG-CoA reductase inhibitors to promote bone formation systemically or at, for example, fracture sites. HMG-CoA reductase is the principal rate limiting enzyme involved in cellular cholesterol biosynthesis. The pathway is also responsible for the production of dolichol, ubiquinones, isopentenyl adenine and farnesol. HMG-CoA reductase converts 3-hydroxy-3-methyld-glutaryl CoA (HMG-CoA) to mevalonate. The '779, '476, and '887 patents do not contemplate use of HMG-CoA reductase inhibitors to promote non-anatomic or heterotopic growth of bone as, for example, in spinal fusion.

SUMMARY OF THE INVENTION

The present invention entails using an HMG-CoA reductase inhibitor to promote nonanatomic or heterotopic growth of bone and aid in bone fusion by promoting bone morphogenetic protein (BMP). The HMG-CoA reductase inhibitor may be, for example, Lovastatin, Simvastatin, Atorvastatin, Pravastatin, or Fluvastatin. Spinal fusion surgery involves adding bone graft, or instrumentation including bone graft, or other implant, to an area of the spine, between two vertebrae, to stimulate a biological bone growth response. The biological response effectively grows the bone graft between the two vertebrae, thereby stopping motion therebetween. The present invention involves administering an HMG-CoA reductase inhibitor to a spinal fusion site to aid that biological response.

Administering an HMG-CoA reductase inhibitor to the site where bone fusion is desired promotes production of BMP at that site by the patient's body. The production of BMP in turn stimulates bone growth and promotes bone fusion. Thus, even though HMG-CoA reductase inhibitors are not themselves osteoinductive, they can successfully be used in promoting non-anatomic or heterotopic growth of bone In addition to use in original spinal fusion surgery, the present invention can be used during revision surgery. A common problem in spine fusion is that it is nonsuccessful and results in non-union. Non-union is particularly difficult to treat and administering an HMG-CoA reductase inhibitor during revision surgery can increase the likelihood of fusion.

The HMG-CoA reductase inhibitor can be administered to the site where bone fusion is desired, such as at the site of vertebral fusion, in any manner appropriate for the particular situation, with preference given to direct delivery to the site. In one embodiment, the HMG-CoA reductase inhibitor is administered to transverse processes during surgery in combination with a carrier. The carrier may be, for example, a porous, open cell matrix formed from collagen fibers coated with resorbable hydroxyapatite. Thus, one possible procedure involves exposing the lamina and transverse processes, decorticating bone, and placing the carrier with HMG-CoA reductase inhibitor in the exposed area.

The carrier may be configured in any suitable manner. Thus, as described above, it may be a collagen matrix with hydroxyapatite. Alternately, it may be a simple collagen or cellular matrix. Further, the carrier may employ covalent or divalent bonding to the HMG-CoA reductase inhibitor. The carrier may also be used in conjunction or as a spinal fusion device such as a cage. In a preferred embodiment, the carrier comprises a noncompressible delivery vehicle.

The carrier may support compounds in addition to the HMG-CoA reductase inhibitor, such as antibiotics, other drugs, or pain medications. The HMG-CoA reductase inhibitor may also be provided in a time release drug delivery system, for example via a hydrogel, polymer membrane, or coating.

In a preferred procedure, the invention involves administering approximately 1–10 mg/kg of Lovastatin via a carrier to a spinal fusion site. The carrier may be a porous, open cell matrix formed from collagen fibers coated with resorbable hydroxyapatite or may be a noncompressible delivery vehicle or other carrier. In an alternate embodiment, the HMG-CoA reductase inhibitor may be administered percutaneously within a supporting compound at the site where bone fusion is desired. Such embodiment promotes BMP production without necessitating surgery.

Thus, the present invention relates to administering a HMG-CoA reductase inhibitor at a site where spinal fusion is desired. The HMG-CoA reductase inhibitor stimulates production of bone morphogenic protein which in turn promotes bone fusion. The HMG-CoA reductase inhibitor may be administered to the site in a variety of different ways including, but not limited to carriers (porous, open cell matrix or other compressible carrier; or non-compressible carrier), time release formulation for use with or without such carrier, or via an injection.

DETAILED DESCRIPTION OF THE INVENTION

The present invention relates generally to spinal fusion and, specifically, to administering an HMG-CoA reductase inhibitor to a surgical site to promote bone fusion. In a preferred embodiment, the invention provides for administering an HMG-CoA reductase inhibitor, for example, Lovastatin, Simvastatin, Atorvastatin, Pravastatin, or Fluvastatin, on a carrier with a noncompressible delivery vehicle for aiding in spinal fusion. Of course, the present invention may be used to promote non-anatomical or heterotopic bone growth between any two bony surfaces where bone growth therebetween is not naturally occurring.

Spinal fusion may be performed for any of a number of reasons. It is frequently used in treatment of a fractured vertebra. Some spinal fractures, including those associated with spinal cord or nerve injury, generally require fusion as part of the surgical treatment. In spondylolisthesis, vertebrae may slip forward on top of one another. This condition may be treated by fusion surgery. Spinal fusion may also be used to correct certain types of spinal deformity such as scoliosis. Another condition treated with fusion surgery is actual or potential instability (or abnormal or excessive motion between two or more vertebrae). Cervical disc herniations requiring surgery often call for fusion as well as removal of the herniated disc (discectomy). With this procedure, the disc is removed through an incision in the front of the neck (anteriorly) and a small piece of bone is inserted in place of the disc. Although disc removal is commonly combined with fusion in the neck, this is not generally the case in the lumbar spine. Further, spinal fusion may be called for in the treatment of a painful spinal condition without clear instability.

Figure 1:
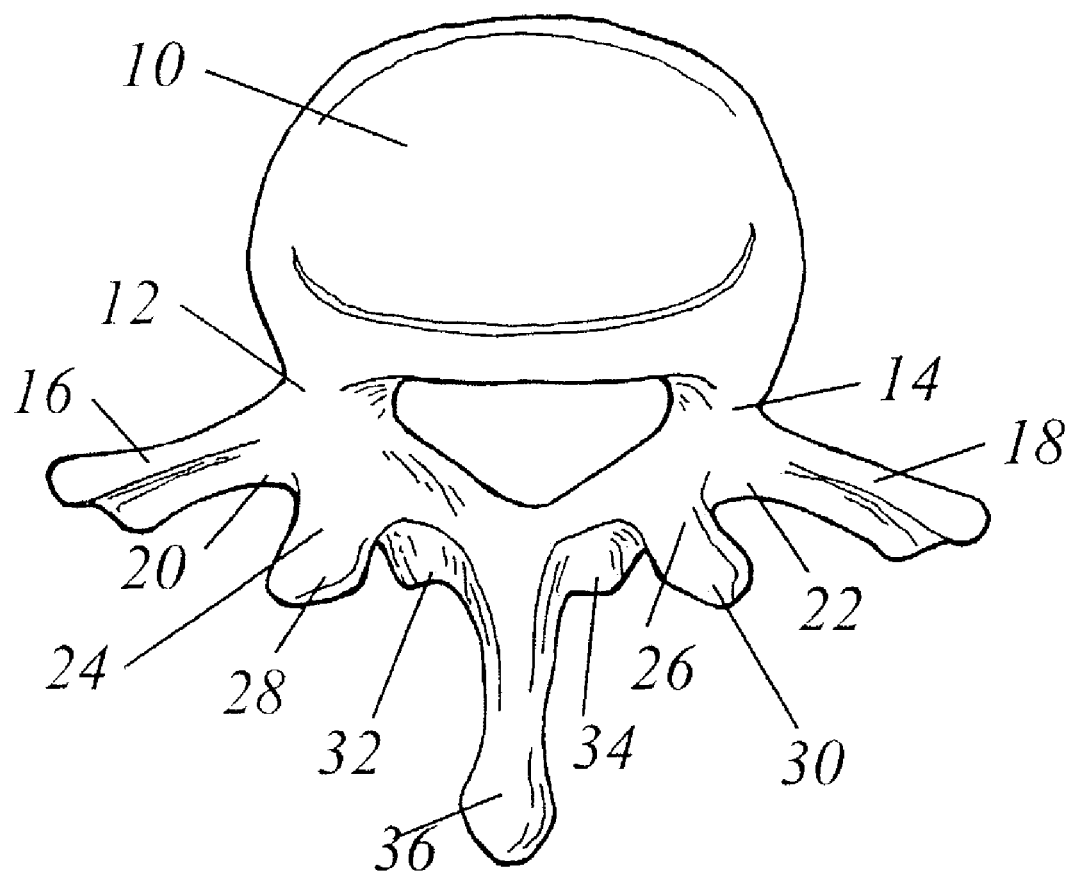
FIG. 1 is a superior view of a $2^{nd}$ lumbar vertebra.

FIG. 1 illustrates a $2^{nd}$ lumbar vertebra as an example vertebra fused using the present invention. The vertebra comprises a vertebral body 10 with first and second pedicles 12 and 14 extending posteriorly therefrom. The pedicles 12 and 14 are strong, cylindrical, anatomic bridges between the dorsal spinal elements and the vertebral body 10. The dorsal spinal elements comprise generally symmetrical transverse processes 16 and 18, accessory processes 20 and 22, superior articular processes 24 and 26, mamillary processes 28 and 30, and laminae 32 and 34 which eventually meet at a single spinous process 36.

Figure 2:
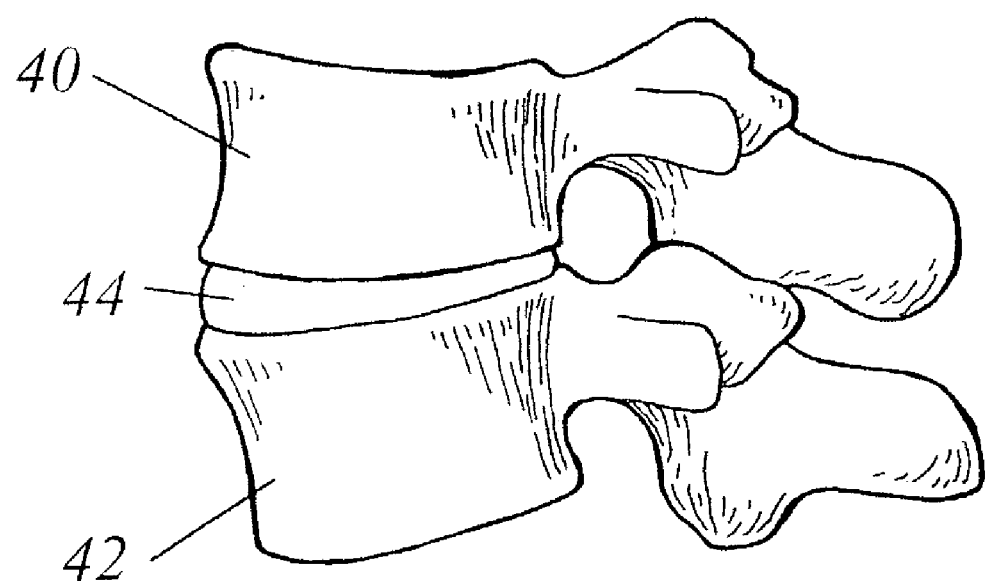
FIG. 2 is a lateral view of the cervical or lumbar spine.

FIG. 2 depicts a lateral view of the cervical or lumbar spine. Top and bottom vertebral bodies 40 and 42 are separated by an intervertebral disc 44. In spinal fusion, bone growth by the top and bottom vertebra is promoted in order to cause the top and bottom vertebra to fuse. The fusion typically involves placement of a bone graft, cage, instrumentation, or other implant, at a site where fusion is desired. The body engages in a natural bone growth healing process. The bone growth results in growth of the bone graft such that the top and bottom vertebrae are fused and motion therebetween is prevented. The bone growth may be between the vertebral bodies, through the intervertebral disc space, between the transverse processes, between the laminae, or between a combination thereof.

In accordance with the present invention, an HMG-CoA reductase inhibitor is placed adjacent to the vertebrae as desired. This may be, for example, adjacent the transverse process, in the intervertebral disc space, or overlying the lamina. A preferred embodiment involves administering approximately 1–10 mg/kg of the HMG-CoA reductase inhibitor, for example, Lovastatin to the site. Local administration of the HMG-CoA reductase inhibitor is preferred and may be performed by conventional methods such as injection at the spinal fusion site, topical application to the site, or time release administration.

Figure 3:
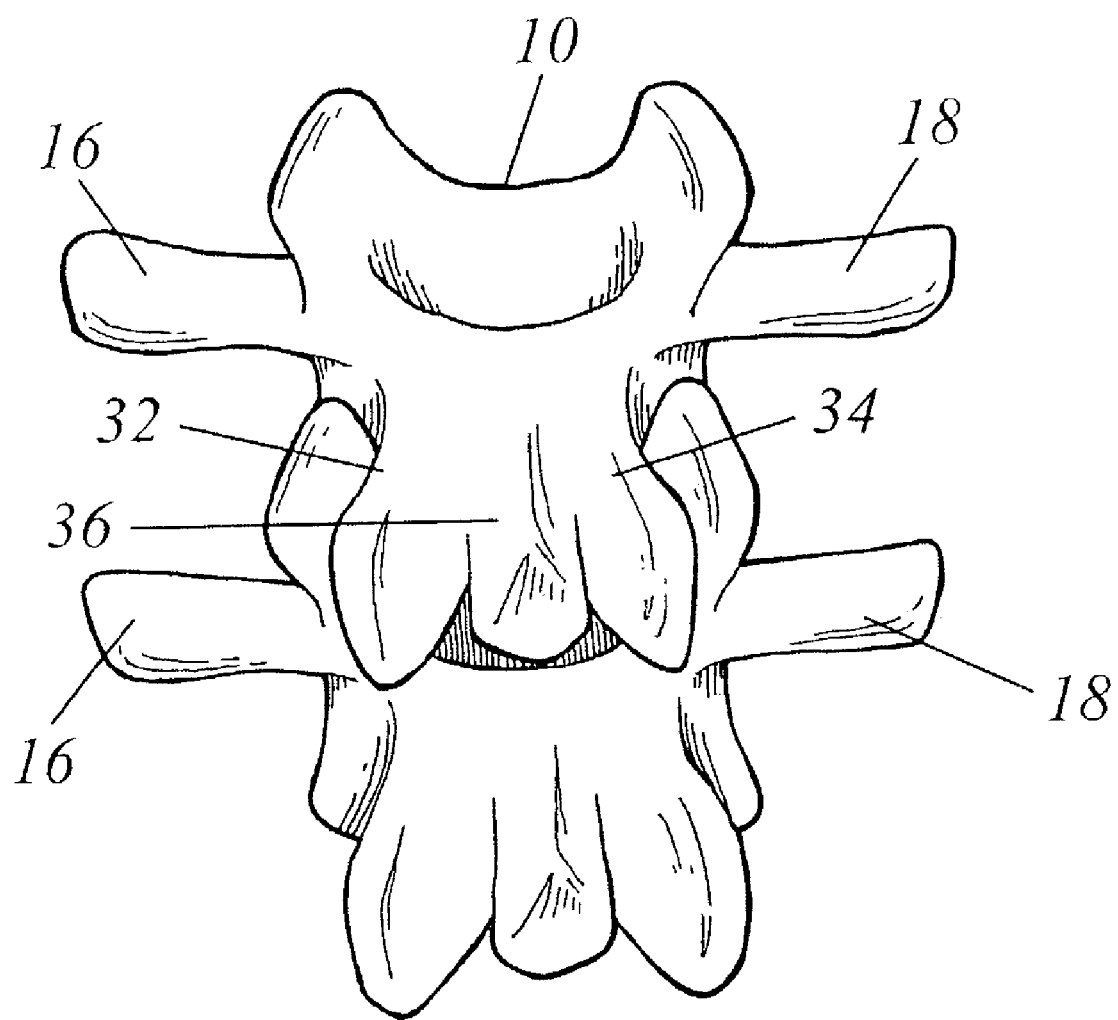
FIG. 3 is a posterior view of the $3^{rd}$ and $4^{th}$ lumbar vertebrae.

FIG. 3 shows a posterior view of the third and fourth lumbar vertebrae. From this perspective, the transverse processes 16 and 18 are more clear. In spinal fusion surgery, the vertebrae may be joined at the transverse processes 16 and 18 of adjacent vertebrae. One possible procedure in accordance with the present invention involves exposing the lamina 32 and 34 and transverse processes 16 and 18, decorticating the bone, and placing a carrier with HMG-CoA reductase inhibitor in the exposed area.

Figure 4:
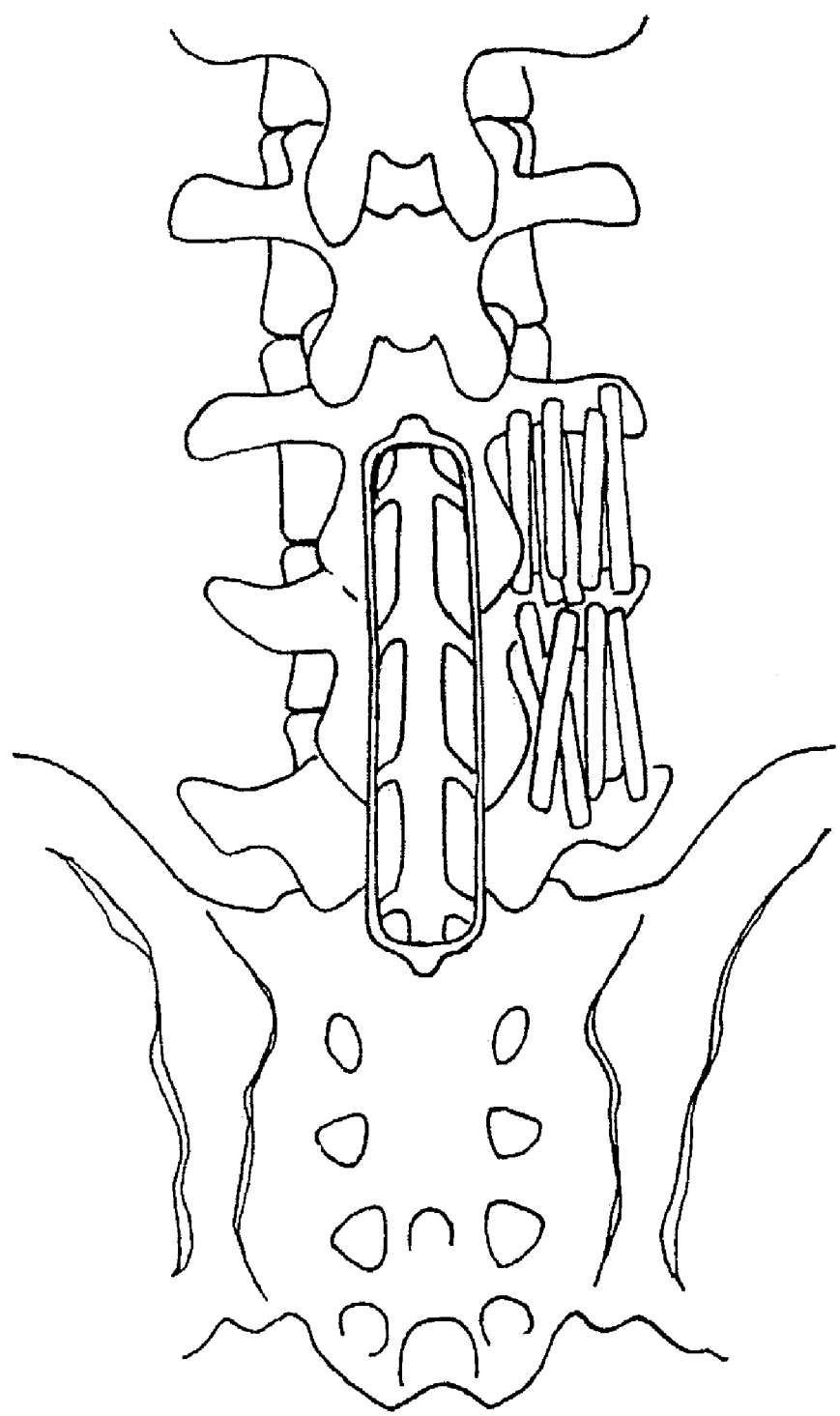
FIG. 4 is a dorsal view of a dorsolateral fusion after total laminectomy.

Preferably, local administration is performed by applying the HMG-CoA reductase inhibitor to a carrier and placing the carrier at the spinal fusion site. FIG. 4 depicts a dorso-lateral fusion after total laminectomy. The fusion bed involves the dorsal aspect of the transverse process, the facet joint, and the pars interarticularis. In one embodiment of the current invention, an HMG-CoA reductase inhibitor is applied to the carrier and the carrier is placed along the decorticated transverse processes. Antibiotics, other drugs, or pain medications may be supported by the carrier. The HMG-CoA reductase inhibitor may also be provided in a time release drug delivery system, for example via a hydrogel, polymer membrane, or coating.

Figure 5:
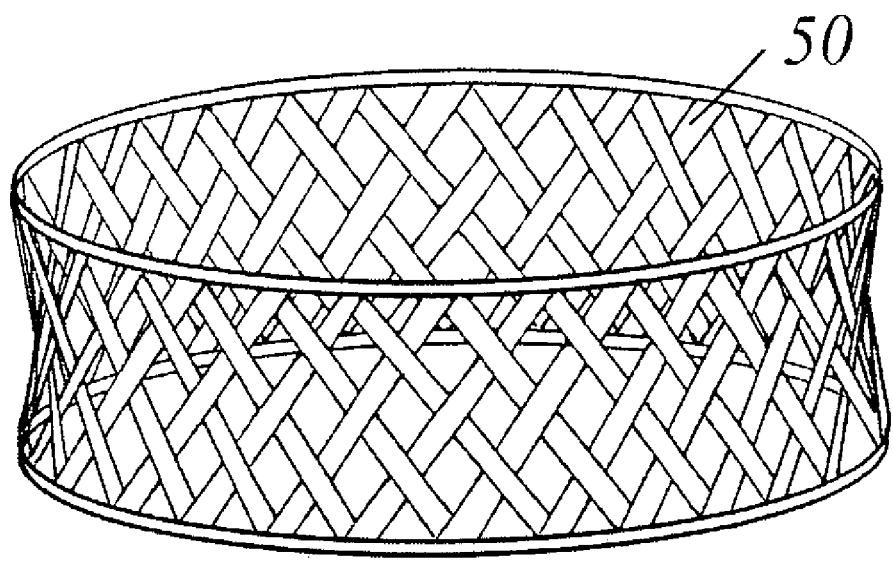
FIG. 5 is a perspective view of a carrier for use with one embodiment of the present invention.

In a preferred embodiment, the HMG-CoA reductase inhibitor is administered to the site via a carrier, for example, a porous, open cell matrix formed from collagen fibers coated with resorbable hydroxyapatite. FIG. 5 illustrates a suitable carrier 50. The carrier 50 may comprise a collagen or cellular matrix. Further, the carrier 50 may employ covalent or divalent bonding to the HMG-CoA reductase inhibitor. The carrier 50 may also be used in conjunction with or as a spinal fusion device such as a cage.

Figure 6:
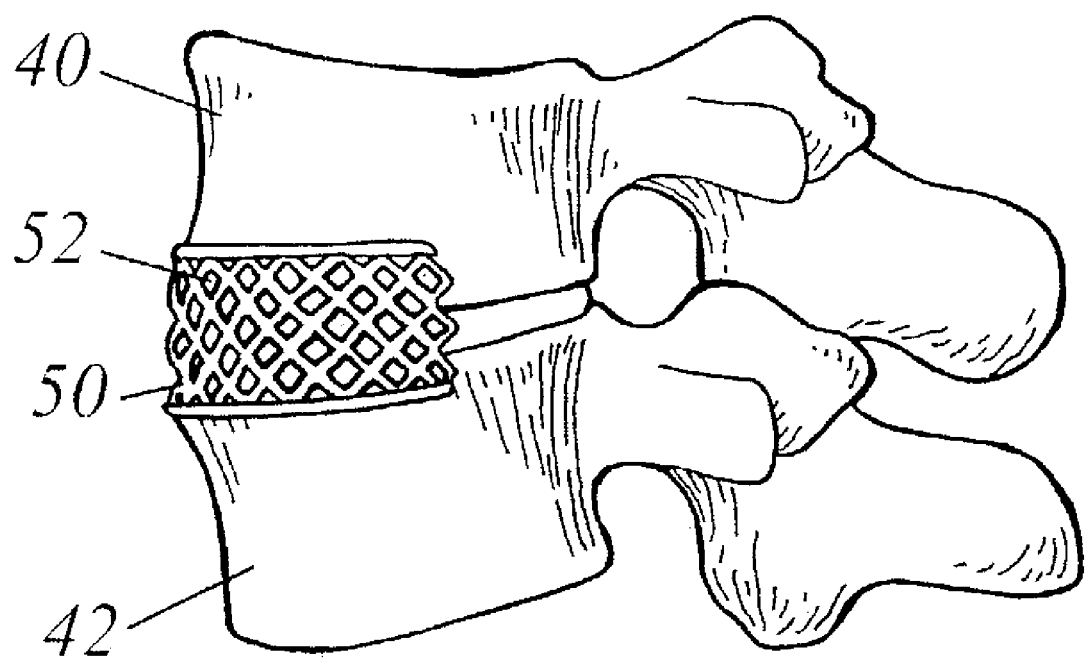
FIG. 6 is a perspective view of a carrier packed in place for spinal fusion in one embodiment of the present invention.

As seen in FIG. 6, the carrier 50 may be packed with HMG-CoA reductase inhibitor 52 and placed in the intervertebral disc space to promote fusion of the vertebra through that space. The HMG-CoA reductase inhibitor is carried to the site by the carrier. Most preferably, the HMG-CoA reductase inhibitor 52 is delivered to the site in conjunction with spinal surgery instrumentation. In a preferred embodiment, the HMG-CoA reductase inhibitor fills the pores of a porous spinal surgery instrumentation device. Thus, the carrier is essentially soaked with HMG-CoA reductase inhibitor that enables a high volume of the HMG-CoA reductase inhibitor to be released. The carrier may further be coated with a time release film.

Figure 7:
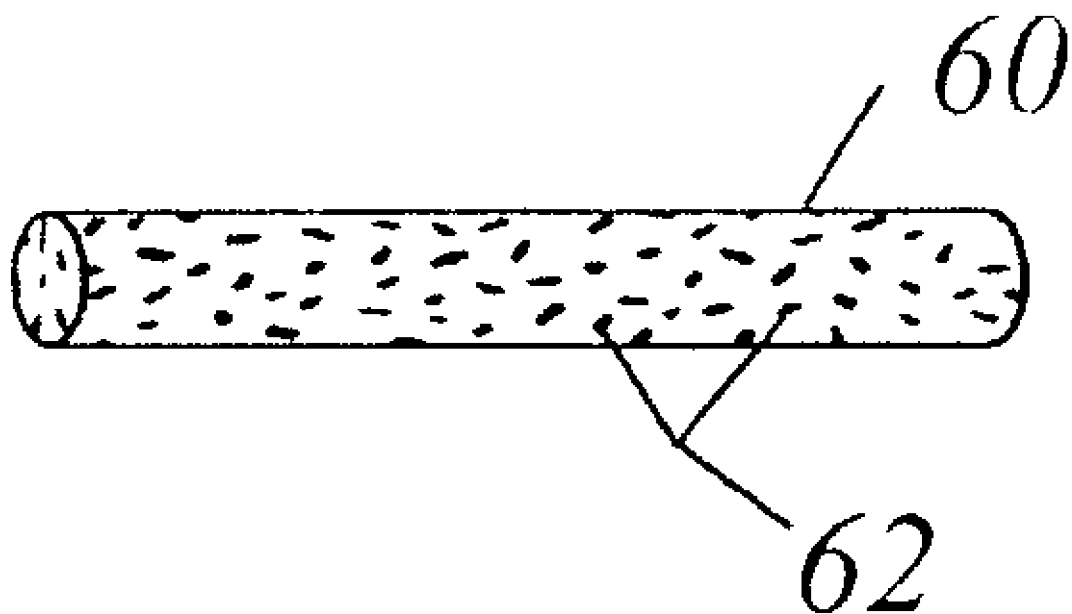
FIG. 7 is a perspective view of an implantation stick in accordance with one embodiment of the present invention.

A further embodiment of the invention includes delivering the HMG-CoA reductase inhibitor to the spinal fusion site with a noncompressible delivery vehicle. The noncompressible delivery vehicle enables a larger volume of bone formation and therefore increases load bearing capacity of the fusion site. FIG. 7 illustrates a non-compressible delivery vehicle in the form of an implantation stick 60. The stick 60 can be hollow or porous and includes a plurality of openings 62. The implantation stick 60 may be packed with an HMG-CoA reductase inhibitor in a time release manner, or with hydroxy appetite.

Figure 8:
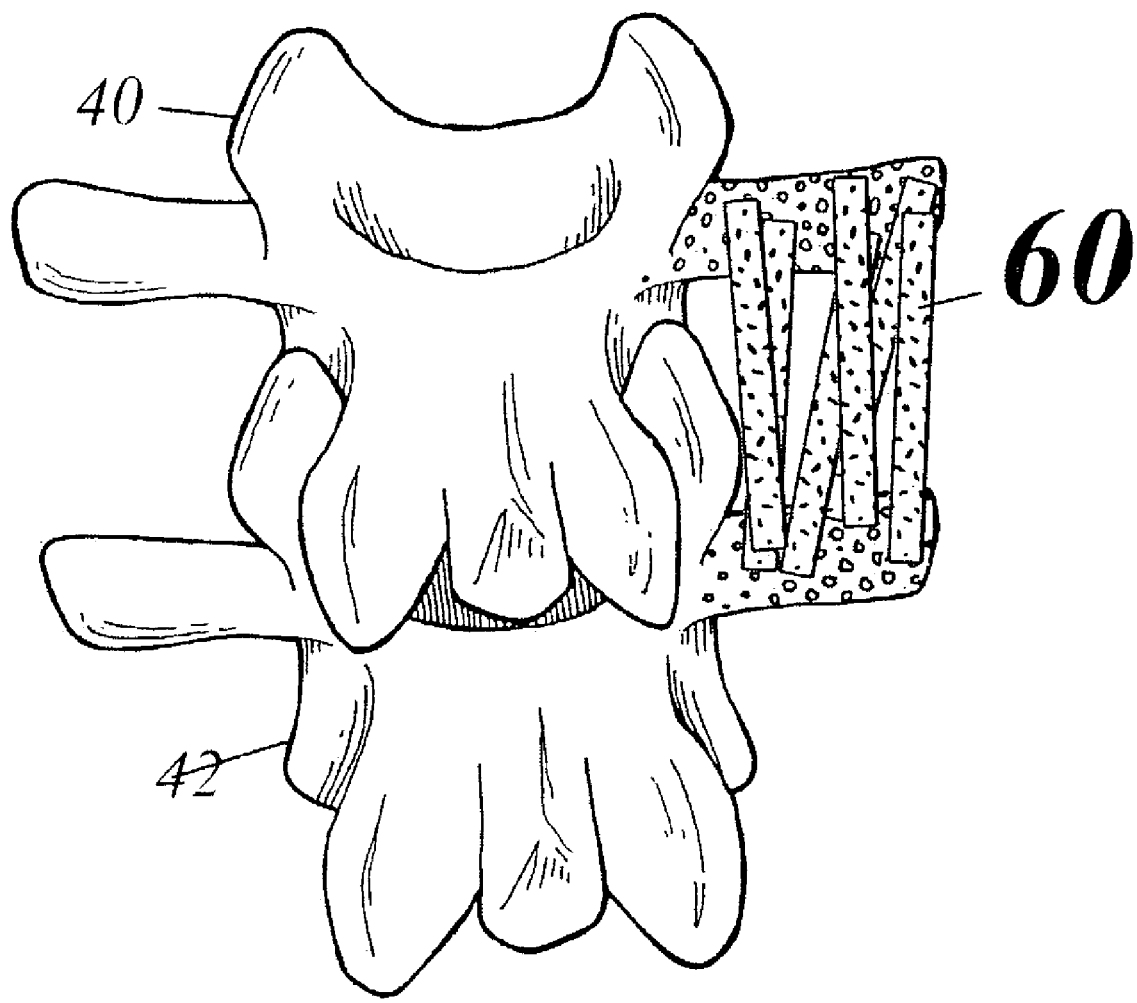
FIG. 8 is a perspective view of posterior lumbar lateral fusion according to one embodiment of the present invention using a plurality of implantation sticks.

FIG. 8 illustrates posterior lumbar lateral fusion according to one embodiment of the present invention using a plurality of implantation sticks 60. In accordance with the present invention, the lamina and transverse process are exposed, bone decorticated, and the carrier with HMG-CoA reductase inhibitor is placed in the exposed area. In the embodiment of FIG. 8, the carrier comprises a plurality of implantation sticks 60 that are placed approximately on the adjacent decorticated lamina and transverse processes bridging the gap between the transverse process of an upper vertebra 40 and the transverse process of a lower vertebra 42. The noncompressible delivery vehicle, for example, the implantation sticks 60, retains a volume between the vertebrae for bone growth. The non-compressible delivery vehicle is packed with an HMG-CoA reductase inhibitor to promote bone growth along the vehicle.

The present invention may involve any suitable instrumentation. For example, a screw may be employed, the screw having an HMG-CoA reductase inhibitor carried thereupon. The screw may comprise a porous material, the HMG-CoA reductase inhibitor being soaked in the pores. Alternately, the screw may be cannulated with the HMG-CoA reductase inhibitor being provided in the hollow opening. Such screws may be used in odontoid screw fixation or c1-c2 transarticular screw fixations. The screw may traverse the fracture site or the joint to produce fusion at the level of the joint.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A method for promoting spinal fusion, the method comprising the steps of: exposing an upper vertebra and a lower vertebra;
   identifying a site for fusion between the upper and lower vertebra;
   exposing a bone surface on each of the upper and lower vertebra at the site for fusion;
   administering an HMG-CoA reductase inhibitor to the site.

2. The method of claim 1, wherein the HMG-CoA reductase inhibitor is Lovistatin.

3. The method of claim 1, wherein the HMG-CoA reductase inhibitor is Statin.

4. The method of claim 1, wherein the HMG-CoA reductase inhibitor is Simvastatin.

5. The method of claim 1, wherein the HMG-CoA reductase inhibitor is Atorvastatin.

6. The method of claim 1, wherein the HMG-CoA reductase inhibitor is Pravastatin.

7. The method of claim 1, wherein the HMG-CoA reductase inhibitor is Fuvastatin.

8. The method of claim 1, wherein the step of administering the HMG-CoA reductase inhibitor further includes the steps of providing the HMG-CoA reductase inhibitor on a carrier and applying the carrier to the site.

9. The method of claim 8, wherein the carrier is an open cell matrix.

10. The method of claim 9, wherein the open cell matrix is formed from collagen fibers.

11. The method of claim 10, wherein the collagen fibers are coated with resorbable hydroxyapatite.

12. The method of claim 8, further including the step of providing a further compound on the carrier.

13. The method of claim 12, wherein the compound is an antibiotic.

14. The method of claim 12, wherein the compound is a pain medication.

15. The method of claim 8, wherein the carrier is a non-compressible delivery vehicle.

16. The method of claim 15, wherein the non-compressible delivery vehicle comprises at least one implantation stick for application to the site such that the implantation stick extends lengthwise between the upper and lower vertebrae.

17. The method of claim 1, wherein the step of administering the HMG-CoA reductase inhibitor includes the step of applying the HMG-CoA reductase inhibitor with a time release drug delivery system.

18. The method of claim 17, wherein the time release drug delivery system comprises a hydrogel.

19. The method of claim 1, wherein the step of administering the HMG-CoA reductase inhibitor includes administering 1–10 mg/kg of the HMG-CoA reductase inhibitor to the site.

20. The method of claim 1, further including the step of providing a bone fusion device to the site.

21. A method for promoting spinal fusion, the method comprising the steps of:
   exposing an upper vertebra and a lower vertebra;
   identifying a site for fusion between the upper and lower vertebra;
   exposing a bone surface on each of the upper and lower vertebra at the site for fusion;
   applying an HMG-CoA reductase inhibitor to a carrier;
   applying the carrier to one of the exposed bone surfaces at the site.

22. The method of claim 21, wherein the carrier is a non-compressible delivery vehicle.

23. The method of claim 22, wherein the non-compressible delivery vehicle comprises at least one implantation stick for application to the site such that the implantation stick extends lengthwise between the upper and lower vertebrae.

24. A method of promoting non-anatomical bone growth between two bony surfaces, the method comprising the steps of:
   identifying a site between two bony surfaces where bone growth is desired but does not
   naturally occur;
   exposing bone at each of the two bony surfaces;
   applying an HMG-CoA reductase inhibitor to at least one of the bony surfaces.

25. The method of claim 24, wherein the step of administering the HMG-CoA reductase inhibitor further includes the steps of providing the HMG-CoA reductase inhibitor on a carrier and applying the carrier to the site.

26. The method of claim 25, wherein the carrier is a non-compressible delivery vehicle.

* * * * *